(12) United States Patent
Escrig et al.

(10) Patent No.: US 6,822,103 B2
(45) Date of Patent: Nov. 23, 2004

(54) INTEGRATED PROCESS FOR SELECTIVE OXIDATION OF ORGANIC COMPOUNDS

(75) Inventors: Pilar De Frutos Escrig, Madrid (ES); Ana Padilla Polo, Madrid (ES); Jose Manuel Riesco Garcia, Madrid (ES); Jose Miguel Campos Martin, Madrid (ES); Gema Blanco Brieva, Madrid (ES); Encarnacion Cano Serrano, Madrid (ES); Mª Del Carmen Capel Sanchez, Madrid (ES); Jose Luis Garcia Fierro, Madrid (ES)

(73) Assignee: Repsol Quimica, S.A., Madrid (ES)

( * ) Notice: Subject to any disclaimer, the term of this patent is extended or adjusted under 35 U.S.C. 154(b) by 0 days.

(21) Appl. No.: 10/453,172

(22) Filed: Jun. 3, 2003

(65) Prior Publication Data

US 2004/0151658 A1 Aug. 5, 2004

(30) Foreign Application Priority Data

Feb. 3, 2003 (EP) ............................................ 03380019

(51) Int. Cl.$^7$ ............................................ C07D 301/12
(52) U.S. Cl. .................... 549/531; 549/523; 423/584
(58) Field of Search ............................... 549/531, 523; 423/584

(56) References Cited

U.S. PATENT DOCUMENTS

| | | | |
|---|---|---|---|
| 2,479,111 A | 8/1949 | Harris | 23/207 |
| 2,869,989 A | 1/1959 | Keeler et al. | 23/207 |
| 2,871,102 A | 1/1959 | Rust et al. | 23/207 |
| 2,871,103 A | 1/1959 | Skinner et al. | 23/207 |
| 2,871,104 A | 1/1959 | Rust | 23/207 |
| 3,156,531 A | 11/1964 | Luten, Jr et al. | 23/207 |
| 3,294,488 A | 12/1966 | Dunlop et al. | 23/207 |
| 4,303,632 A | 12/1981 | Gosser | 423/591 |
| 4,681,751 A | 7/1987 | Gosser | 423/584 |
| 4,701,428 A | 10/1987 | Bellussi et al. | 502/8 |
| 4,772,458 A | 9/1988 | Gosser et al. | 423/584 |
| 4,824,976 A | 4/1989 | Clerici et al. | 549/531 |
| 4,832,938 A | 5/1989 | Gosser et al. | 423/584 |
| 4,897,252 A | 1/1990 | Cochran et al. | 423/591 |
| 4,937,216 A | 6/1990 | Clerici et al. | 502/62 |
| 4,975,266 A | 12/1990 | Albal et al. | 423/591 |
| 5,166,372 A | 11/1992 | Crocco et al. | 549/531 |
| 5,214,168 A | 5/1993 | Zajacek et al. | 549/531 |
| 5,254,326 A | 10/1993 | Leyshon et al. | 423/591 |
| 5,338,531 A | 8/1994 | Chuang et al. | 423/584 |
| 5,912,367 A | 6/1999 | Chang | 549/529 |
| 5,968,472 A | 10/1999 | Oyague et al. | 423/591 |
| 6,168,775 B1 | 1/2001 | Zhou et al. | 423/584 |
| 6,387,346 B1 | 5/2002 | Bertsch-Frank et al. | 423/584 |
| 6,500,968 B2 * | 12/2002 | Zhou et al. | 549/531 |
| 2001/0016187 A1 | 8/2001 | Zhou et al. | 423/582 |
| 2003/0215383 A1 | 11/2003 | Escrig et al. | |

FOREIGN PATENT DOCUMENTS

| | | |
|---|---|---|
| CA | 560133 | 7/1958 |
| EP | 0 378 388 A1 | 7/1990 |
| EP | 0 492 064 A1 | 9/1991 |
| EP | 492064 A1 * | 7/1992 |
| EP | 0 504 741 A1 | 9/1992 |
| EP | 0 978 316 A1 | 2/2000 |
| EP | 1 074 548 A1 | 2/2001 |
| GB | 758907 | 10/1956 |
| GB | 759464 | 10/1956 |
| WO | 94/23834 A1 | 10/1994 |
| WO | 99/41190 A1 | 8/1999 |
| WO | 99/48884 A1 | 9/1999 |
| WO | 01/05498 A1 | 1/2001 |
| WO | 01/05501 A1 | 1/2001 |

OTHER PUBLICATIONS

U.S. patent application Ser. No. 08/960,857, Oyague et al., filed Oct. 30, 1997.

Letters ("Handling Hazardous Chemicals," "Nominal and Actual Molarity," & "Thanks to Younger Chemists") *Chemical and Engineering News*, p. 4 (Jan. 7, 1985).

MacKenzie, J., "Hydrogen Peroxide Without Accidents," *Chemical Engineering*, pp 84–90 (Jun. 1990).

Milas, N.A., et al., "Studies in Organic Peroxides. XXVI. Organic Peroxides Derived from Acetone and Hydrogen Peroxide," *J. Am. Chem. Soc.*, vol. 81, pp 6461–6462 (1959).

Schwoegler, E.J., Letter entitled "Shock Sensitivity of Acetone Peroxides," *Chemical and Engineering News*, p. 4 (Jan. 7, 1985).

* cited by examiner

*Primary Examiner*—Ba K. Trinh
(74) *Attorney, Agent, or Firm*—Ladas & Parry LLP

(57) ABSTRACT

Oxidized compounds are produced in a continuous integrated process in liquid phase, which comprises: Step I, synthesis of non acidic hydrogen peroxide solutions by direct reaction between hydrogen and oxygen by catalytic reaction utilizing a noble metal catalyst. Step II, this hydrogen peroxide solution is directly mixed with an organic substrate, a suitable catalyst and optionally a solvent. The integrated process requires no treatment step and is particularly well adapted to the production of propylene oxide.

20 Claims, 1 Drawing Sheet

INTEGRATED PROCESS FOR SELECTIVE OXIDATION OF ORGANIC COMPOUNDS

FIELD OF THE INVENTION

The invention refers to on integrated process for selective oxidation of organic compounds, in liquid phase, which comprises a first step for direct synthesis of a non acidic hydrogen peroxide solution and a second step for oxidation an organic substrate with the reaction mixture of the first step.

STATE OF THE ART

Selective oxidation reactions are a major class of chemical transformations which account for the production of a wide variety of important chemical products, including alcohols, carbonyl compounds, epoxides, hydroxylates, acids, glycols and glycol ethers, lactones, oximes, and oxygenated sulfur and nitrogen compounds such as sulfoxides, sulfones, nitrones, azo compounds, and other N-oxides. Performing these chemical transformations efficiently, economically, and safely requires a suitable oxidizing agent which can be purchased or produced to react with the desired organic chemical feedstock, which is then converted to the oxidized organic chemical product.

Several significant problems face conventional oxidation processes. Some industrial processes use gas containing oxygen such as air or pure oxygen. But using oxygen combined with organic chemical feedstocks may accidentally achieve gas compositions in the explosive range, thereby posing a serious safety hazard. Such oxidation processes can also be prone to forming explosive gas mixtures. Oxidative processes using oxygen or air also tend to suffer from product selectivity problems related to overoxidation of the organic chemical feedstock, normally producing undesired carbon oxides (CO, $CO_2$)

An attractive alternative to using oxygen or air as the oxidation agent is the use of organic hydroperoxides as oxidizing agents. These hydroperoxide compounds, typically generated by oxidation of suitable intermediates with air or $O_2$, are reacted with chemical feedstocks to form oxygenated products and organic by-products. The most common processes for producing propylene oxide (PO) use tert-butyl hydroperoxide and ethylbenzene hydroperoxide as hydroperoxides. These processes cause the formation of a higher quantity of co-products of commercial interest with respect to PO. For example, the process via tert-butyl hydroperoxide co-produces 2.5–3.5 kg of tert-butyl alcohol per kg of PO, whereas via ethylbenzene hydroperoxide co-produces 2.2–2.5 kg of styrene per kg of PO. The presence of these co-products can be of little advantage if the request for PO and the respective co-products is not suitably balanced. For example, when the demand for styrene, or methyl tert-butyl ether (MTBE) which could be obtained from tert-butyl alcohol, is high, the economics of this process are competitive; otherwise these processes are not economic.

Instead of using organic peroxides, hydrogen peroxide is a known desirable oxidizing agent. The byproduct of oxidation reactions using hydrogen peroxide is typically water, a safe compound that can be easily recovered and reused or disposed. The amount of water on a weight basis is much less than the amount of organic by-product when organic hydroperoxides are used, and thereby represents significant savings in process costs. However, past attempts to develop selective chemical oxidation processes based on hydrogen peroxide have encountered significant difficulties. Conventional hydrogen peroxide production utilizes the anthraquinone process, wherein the anthraquinone is first hydrogenated to anthrahydroquinone and then autoxidized to release hydrogen peroxide and the anthraquinone for recycle. Hydrogen peroxide is generated at low concentrations in the solution, and very large flows of anthraquinone and anthrahydroquinone must be handled in order to produce the desired hydrogen peroxide product. Accordingly, such conventionally produced hydrogen peroxide is generally too expensive for commercial use as an oxidizing agent for selective chemical oxidation processes.

A second method for the production of hydrogen peroxide comprises the use of secondary alcohols such as isopropanol and methylbenzylalcohol (U.S. Pat. No. 2,871,102, EP 378388, EP 1074548) or high-boiling secondary alcohols such as diaryl methanol (U.S. Pat. No. 4,303,632) with oxygen. These known processes, however, substantially suffer from disadvantages deriving from the necessity of operating at high reaction temperatures (generally ranging from 100 to 180° C.), the partial oxidation of the ketone which is formed as main co-product, the necessity of using a hydrogen peroxide stabilizer (orthophosphoric acid or sodium pyrophosphate). Furthermore, these processes are complicated by the necessity of separating and recovering the cetone and by products from the reaction mixture after using the hydrogen peroxide solution in a subsequent epoxidation process.

An important alternative is generating hydrogen peroxide directly by the catalytic reaction of hydrogen and oxygen, which avoids the difficulty of accompanying large flows of a working solution and can reduce the cost of hydrogen peroxide. These processes generally use a catalytic system consisting of a noble metal, particularly metals of the platinum group or their mixtures, in the form of salts or as supported metals, by reacting the two gases in a solvent consisting of an aqueous medium or an aqueous organic medium. The prior art includes a number of catalytic technologies which directly convert hydrogen and oxygen to hydrogen peroxide, but generally utilize a hydrogen/oxygen feed wherein the hydrogen concentration is greater than about 10 mol % (U.S. Pat. Nos. 4,681,751, 4,772,458, 4,832,938, 5,338,531), which is well above the flammability limit of 4.5 mol % for such mixtures and creates a serious process hazard. At hydrogen feed concentrations below 4.5 mol %, the prior art catalysts are not sufficiently active and selective to generate hydrogen peroxide product at a reasonable rate (WO 99/41190, WO 01/05498 WO 01/05501, U.S. Pat. No. 6,168,775 B1). The prior art technologies need the use in the reaction medium of high concentrations of promoters, for example acid promoters, halogenated products and/or other additives. This makes it necessary to add stabilizers, with onerous purification operations of the $H_2O_2$ solution before its use in the oxidation reactions.

Various oxidation processes for organic chemical feedstocks utilizing hydrogen peroxide are known. For example, U.S. Pat. No. 4,701,428 discloses hydroxylation of aromatic compounds and epoxidation of olefins such as propylene with H2O2 using a titanium silicalite catalyst. Also, U.S. Pat. Nos. 4,824,976; 4,937,216; 5,166,372; 5,214,168; 5,912,367, WO 94/238234 and WO 99/48884 all disclose epoxidation of various olefins including propylene using titanium compounds catalysts.

EP 978316 describes a process for catalytic oxidation of an organic compound selected from olefins, aromatic hydrocarbons, ammonia and carbonyl compounds, including a first step for direct synthesis of hydrogen peroxide using a metal of group VIII supported on activated carbon functionalized with sulfonic acids, and a second step for oxidation of said organic compound substrate with the reaction mixture from the first step containing hydrogen peroxide to obtain the desired oxidized product. When the olefin is propylene, the best overall yield of propylene oxide, based on hydrogen feed, that can be achieved is 83%. However, higher yields of oxidized organic compounds are much desired.

U.S. 2001/0016187 describes a process for selective oxidation of organic chemical feedstocks utilizing directly produced hydrogen peroxide intermediate oxidant, including a first step for direct synthesis of hydrogen peroxide using a supported phase-controlled noble metal catalyst, namely a Pd/carbon black catalyst, in a solvent, in the presence of acid promoters and/or stabilizers, such as sulfuric acid, and a second step for oxidation of said organic compound substrate with the reaction mixture from the first step containing hydrogen peroxide to obtain the desired oxidized product. No data concerning oxidation of any organic chemical feedstock is provided.

SUMMARY OF THE INVENTION

The present invention provides an integrated process for the oxidation of organic compounds comprising the following steps: Step I, production of hydrogen peroxide from hydrogen and oxygen in the presence of a solvent and a catalyst comprising at least a noble or semi-noble metal supported on a halogen free acid resin; and Step II, wherein the hydrogen peroxide solution is directly mixed with an organic substrate, a suitable catalyst and optionally a solvent to produce the corresponding oxidized compound. The integrated process requires no treatment step and is particularly well adapted to the production of propylene oxide.

Figure 1:
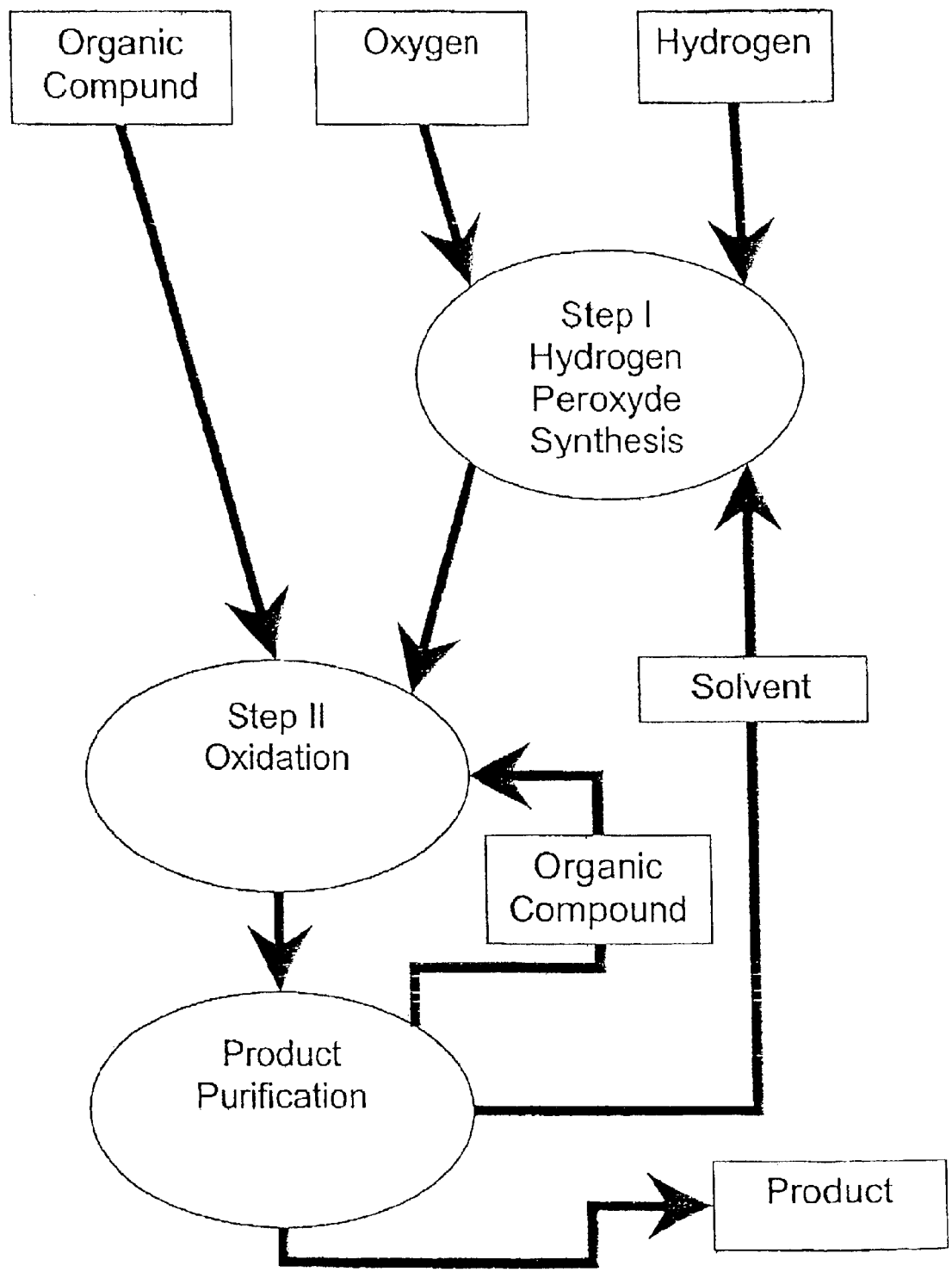
FIG. 1 provides an overview of a preferred embodiment of the continuous, integrated process of the invention. The scheme for organic compounds oxidation, using hydrogen peroxide generated by direct reaction of oxygen and hydrogen is illustrated in the Figure. In the first step hydrogen and oxygen (as purified oxygen or air) are reacted over the supported noble metal catalyst in the presence of a liquid solvent in a first reactor or in a first chamber of a twin-chambered tank reactor to generate a liquid solution of hydrogen peroxide. The reaction mixture resulting from this first step is combined, in the second step of the process, in a second reactor or in a second chamber of a twin-chambered tank reactor, with an organic compound which undergoes oxidation.

The reaction mixture from the second step is then fractionated by any of the means that are standard within the art. As a result of the fractionation, unreacted organic compound may be purified and recycled back to the corresponding reactor or chamber. The fractionation process may also provide for isolation of the solvent used in the hydrogen peroxide synthesis. Such fractionation may be employed as a secondary procedure, or as an integral part of the product purification (as illustrated in FIG. 1). This solvent isolated in the fractionation procedure may be recycled for further use.

The figure portrays reagents within boxes, and reactions within elipses. The arrows indicate ingredients required and/or generated by the individual steps of the procedure. The major reagents and reactions are shown in bold typeface, as are the arrows depicting the major additions (ingredients required) and products (ingredients generated) associated with the individual steps of the process.

DETAILED DESCRIPTION OF THE INVENTION

The present invention provides an effective process for selective oxidation of organic chemical compounds with directly produced hydrogen peroxide, comprising the following steps:
(i) preparing a non acidic hydrogen peroxide solution by reacting hydrogen and oxygen in a solvent, in the presence of a first catalyst comprising at least a noble metal or semi-noble metal belonging to groups VII to XI of the periodic table supported on a halogen-free acid resin:
(ii) recovering the reaction mixture of step (i) containing said non acidic hydrogen peroxide solution; and
(iii) contacting said non acidic hydrogen peroxide solution with an organic chemical compound, in the presence of a second catalyst to render an oxidized product.

The reaction solution of the first reaction (hydrogen peroxide synthesis) may be used directly as a reagent for the second reaction (oxidation). There is no requirement for purification or enrichment of intermediates, or for the removal of by-products from the production of hydrogen peroxide. The second reaction uses the products of the first reaction to oxidize an organic substrate at moderately elevated temperature and pressure. This oxidation reaction is performed in the presence of suitable catalysts. The oxidized product may be recovered from the reaction medium of the second reaction.

The expression "non acidic hydrogen peroxide solution", as used in the present description, means that although a catalitical amount of an acid promoter, e.g. HBr, is used in the direct synthesis of hydrogen peroxide from hydrogen and oxygen in a solvent, said compound is added in an amount such that is not sufficient to render acidic the pH of the resultant hydrogen peroxide solution.

According to the present invention, the coupled hydrogen peroxide generating reaction and oxidation reaction may be performed in a continuous manner, using on appropriate reactor, such as, a twin-chambered tank reactor for example, permitting controlled addition of the hydrogen peroxide containing reaction mixture from the first reaction (in the first chamber) into a second chamber. This second chamber would house the oxidation reaction, with forced mixing of the contents and agitation therein of a suspension of catalyst particles. Reactant solutions may be added in combination or sequentially. For example, either the reaction mixture generating hydrogen peroxide, or the organic chemical compound, for example an olefin, or both of these reagents may be added to the reactor incrementally.

The oxidation product may be separated from the oxidation reaction mixture by standard methods known in the art, such as liquid-liquid extraction, extraction by distillation or fractional distillation. These operations may be performed on the entire reaction mixture, and may follow removal of said second catalyst. Alternatively, the oxidized product may be separated from part or all of the reaction mixture according to a periodic program, or from a part of the reaction as a component of a continual operation.

Other components of the oxidation reaction mixture may be isolated by recognized means of fractionation, such as differential distillation, either as part of the process of purifying the product or as a distinct fractionation procedure, preceding or following removal of the oxidized product. The solid catalyst may be separated from the oxidation reaction mixture for regeneration by methods well known in the art, such as filtration. Regeneration of the catalyst is described in greater detail below.

The integrated process for the industrial oxidation of organic compounds that is provided by the invention solves a similar problem to that addressed, in part, by the integrated procedures disclosed in the prior art as described above. In addition, the present invention incorporates improvements to the component reactions of the integrated process which increase their rate, selectivity and compatibility, resulting in significant enhancement of the process as a whole. Certain of these improvements, such as the use into the peroxide-generating reaction of halogen-free acidic resin supported noble metal catalyst can get non-acidic hydrogen peroxide solutions which can be used directly in the oxidation reaction step without any purification or additive feed benefit the overall efficiency of the integrated process.

In particular, the distinctions that differentiate the present invention from U.S. patent application No. 2001/016187 which also discloses an integrated process for oxidizing organic feedstocks, illustrate significant advantages of the present invention:

i. By improving the activity of the peroxide-generating reaction the present invention permits greater concentrations of hydrogen peroxide to be generated in the first reaction mixture which is then used as oxidant solution for the oxidation reaction. The overall yield and efficiency of the process may therefore be increased, provided that the hydrogen peroxide at these elevated concentrations can be maintained in solution by the selected organic solvent and can be prevented from reacting with other components of the reactions making up the integrated process. The current invention successfully addresses each of these requirements.

ii. High concentrations of acid promoters such as inorganic acids (sulfuric, phosphoric, nitric, . . . ) or organic acids (per example, sulphonic acids) are not required in the hydrogen peroxide generation reaction, avoiding the production of acidic hydrogen peroxide solutions that are corrosive and require the use of special equipments.

iii. The ability to use the reaction mixture from the first step directly as an ingredient of the second reaction, providing the peroxide for the oxidation, permits great advantages in efficiency and cost-effectiveness, since no intermediate step is required in order to purify or neutralize the peroxide.

Hydrogen peroxide synthesis and oxidation steps will be described in a detailed manner below.

Hydrogen Peroxide Synthesis Step

In this step, hydrogen and oxygen (as purified oxygen or air) are reacted continuously over the supported noble metal or semi-noble metal catalyst in the presence of a liquid solvent in a reactor to generate a liquid solution of non acidic, hydrogen peroxide. The reactor may contain a fixed, fluidized or slurried bed of the catalyst. The liquid medium may be water, or a suitable organic solvent such as an alcohol, for example, a $C_1$–$C_{12}$ alcohol, a $C_1$–$C_{12}$ glycol, or mixtures thereof. Suitable organic solvents can include various alcohols, aromatics, and esters, or any other organic compound that is inert in reaction conditions. Solvents are preferably water-soluble alcohols such as methanol, ethanol, n-propanol, isopropanol, tert-butanol, isobutanol and mixtures thereof. In a particular embodiment, the solvent is selected from the group formed by water, $C_1$–$C_{12}$ alcohols, $C_1$–$C_{12}$ glycols, and mixtures thereof. The hydrogen concentration in the reactor is maintained below the flammability limit of about 4.5 mol %. The liquid-phase concentration of hydrogen peroxide intermediate product can vary over a useful range of 1–30 wt %. The optimum hydrogen peroxide concentration depend on a variety of factors, including hydrogen cost, separation requirements, and optimal peroxide concentration for best performance of the downstream oxidation reactor. In general, the preferred $H_2O_2$ concentration will be 1–25 wt %, and more preferably will be 5–20 wt %.

The catalyst used in the first step is a halogen-free acidic resin-supported noble or semi-noble metal catalyst that selectively produces essentially only the hydrogen peroxide intermediate, as disclosed in our pending European patent application No. 02380057.6. The halogen-free acidic resin supported noble metal catalyst has been experimentally proved to directly produce hydrogen peroxide at very high selectivity. By using this catalyst in a reactor and at reaction conditions of $-10°$ C. to $100°$ C., preferably $10$–$75°$ C., at a pressure above atmospheric pressure, typically comprised between 2 and 30 MPa, optionally in the presence of an inert gas, the process first reaction step will produce hydrogen peroxide intermediate at very high selectivity, typically, equal to or higher than 80%.

The molar ratio hydrogen/oxygen can vary in a brood range and is preferably comprised between 1/1 and 1/100, more preferably between 1/10 and 1/50.

The support employed in the catalyst used in the process of this invention comprises a resin functionalized with halogen-free acid groups. Preferably, the resins used in the preparation of the catalyst to be used in the first reaction are formed by homopolymerization of monomers or copolymerization of two or more monomers. Examples of resins suitable as a support in the present invention include styrenic, acrylic, methacrylic polymers or styrene-divinylbenzene copolymers. These resins are preferably functionalized with halogen-free acid groups such as sulphonic, carboxylic, dicarboxylic, etc. (Encyclopedia of Chemical Technology Kirk Othmer $3^{rd}$ Edition, Vol. 13, p 678–705, Wiley-Interscience, John Wiley and Sons, 1981). Furthermore the resins used in the present invention can have an inorganic part, e.g. the resin is deposited onto an inorganic solid.

In a particularly preferred embodiment, the hologen-free acid resin is a sulphonated styrene-divinylbenzene copolymer resin.

The catalyst of the first reaction comprises at least a noble metal or semi-noble metal selected from groups VII to XI of the periodic table supported on the above resin.

Preferably, said noble or semi-noble metal is selected from the group consisting of palladium, platinum, silver, gold, rhodium, iridium, ruthenium, osmium, and mixtures thereof. Most preferred metal is palladium, optionally in combination with other metal cited.

The catalyst is preferably prepared by adding a noble metal or semi-noble metal belonging to groups VII to XI of the periodic table, preferably palladium, platinum, silver, gold, rhodium, iridium, ruthenium, osmium, or mixtures of two or more of these metals, to the non-halogenated acid resin. The amount of metal supported can vary in a broad range, but is preferably comprised between 0.001 and 20% with respect to the non-halogenated acid resin, more preferably between 0.1 and 10%.

The addition of the metal to the support can be performed using any of the known preparation techniques of supported metal catalyst, e.g. impregnation, adsorption, ionic exchange, etc. For the impregnation, it is possible to use any kind of inorganic or organic salt of the metal to be impregnated that is soluble in the solvent used in the addition of the metal. Suitable salts are for example acetate, nitrate, halide, oxalate, etc.

In a particular embodiment, the first step comprises:
a) feeding to a reactor, containing the catalyst in a fixed bed or dispersed in a liquid medium:
   a1) a liquid stream consisting of an alcohol or an alcohol-water mixture, and
   a2) a gaseous stream containing hydrogen and oxygen, and optionally an inert gas, wherein the concentration of hydrogen is lower than 4.5% by volume: and
b) removing from the reactor:
   b1) a liquid stream substantially consisting of the stream a1 and also the hydrogen peroxide and water produced by the reaction; and
   b2) a gaseous stream consisting of the non-reacted gases and eventual inert gases.

When the first reaction is performed in a slurry reactor, the catalyst is preferably removed from the hydrogen peroxide solution stream using the techniques known in the art such as decantation, centrifugation, filtration, etc. In the preferred embodiment of the invention wherein the catalyst is used in fixed bed, obviously, the separation step is not necessary.

Although not necessary, in some cases it may be desirable to remove a portion of the solvent or water from the first reactor effluent to generate a more concentrated hydrogen peroxide solution.

The final non acidic hydrogen peroxide solution is passed on to a second catalytic reaction step.

Oxidation Step

The reaction mixture containing hydrogen peroxide from the hydrogen peroxide synthesis reaction is used as the oxidant for the oxidation reaction in which an organic compound undergoes oxidation by the hydrogen peroxide in the presence of a catalyst. The ability to use the reaction mixture from the first step directly as an ingredient of the second reaction, providing the peroxide for the oxidation, permits great advantages in efficiency and cost-effectiveness, since no intermediate step is required in order to purify the peroxide.

A variety of organic chemical compounds can be used in the overall process of the instant invention in order to produce the desired oxidized organic chemical compounds. Major classes of organic chemical compounds include aromatics, alkanes, carbonyl compounds and olefins, as well as compounds containing mixed functionality and heteroatoms such as sulfur or nitrogen, with the olefin compounds being preferred. The major groups of oxidized organic chemical compounds are alcohols, epoxides, carboxylic acids, hydroxylated aromatics, aldehydes/ketones, glycols, oximes and N-oxides.

Some important specific and preferred organic chemical compounds and their corresponding oxidized products which may be processed by the two-step selective catalytic oxidation process of this invention utilizing hydrogen peroxide intermediate as the oxidant are listed below;

| | |
|---|---|
| Propylene | Propylene Oxide |
| Allyl Alcohol | Glycidol |
| Allyl Chloride | Epichlorohydrin |
| Cyclohexene | Cyclohexene Oxide |
| Cyclohexanone | Cyclohexane Oxime |
| Benzene | Phenol |
| Phenol | Hydroquinone and Pyrocatechol |

Olefins are more preferred organic compounds, with propylene being the most preferred feedstock for producing propylene oxide.

The non acidic hydrogen peroxide solution obtained in the first step and an additional solvent, if it is desirable, are fed, preferably continuously, together with a selected organic chemical feedstock into a catalytic reactor, which may be a fixed bed or slurry-type reactor containing a known oxidation catalyst such as TS-1, TS-2, Tiβ, Ti-MCM-41, titanium on amorphous silica, etc., or any known catalyst capable of oxidizing efficiently organic compounds with hydrogen peroxide. For a fixed bed reactor, the preferred catalyst particle size will be 0.5–20 mm, and for a fluidized or slurry reactor the preferred catalyst size will be 50–1,000 microns. The reactor is maintained at about −30° C. to 200° C. of temperature, preferably at −10° C. to 100° C. temperature. The oxidation reaction is carried out at a pressure, usually above atmospheric pressure, enough to keep the organic feedstock in the liquid phase. In a particular embodiment, the oxidation reaction is carried out at a pressure between 0.1 and 10 MPa, preferably, between 0.1 and 5 MPa. If the reactor is of the slurry type, the effluent liquid stream removed from the reactor will contain unreacted feedstocks, solvent and catalyst particles, and preferably the catalyst should be recovered by centrifugation, filtration or any adequate means and reused. For fixed bed reactors, no catalyst recovery and recycle is needed. Following any catalyst recovery, the remaining liquid stream is passed to organic feedstock recovery; this unreacted organic compound could be recycled back to the reactor together with make up feedstock supplied. The unreacted organic compound recovery step may be carried out in a single distillation tower or it may include sequential distillation towers operated at progressively lower pressures as desired.

The remaining stream is passed to product purification, where product is removed for further purification as desired. Solvents and any heavy fractions are passed to a solvent recovery unit. The solvent fed to the organic compound oxidation, if it is necessary, is recycled back to the oxidation reactor. The liquid solvent employed in the hydrogen peroxide solution are recycled back to the first step, while heavy fractions and the net water produced in reactor are withdrawn for other use or disposal.

Any useful process schemes or sequences for oxidized product purification and recovery are also possible as will be understood by those skilled in this art will be applied to this invention.

In order to illustrate the nature of the invention more fully, and the manner in which it is to be practiced, the following examples are presented:

EXAMPLES

Example 1

A catalyst was prepared from a commercial resin functionalized with sulphonic groups (Lewatit® K2641 Bayer AG, non-halogenated macroporous resin, with an exchange capacity of 4.8 eq/l, pore diameter 70 nm, porosity 0.3 ml/g, and a specific surface area BET 35 m$^2$/g). Firstly the resin was washed three times with acetone, using equal volumes of solvent and resin. Next, a resin suspension (4 g) is prepared with 50 ml of methanol. To this suspension, a palladium (II) acetate solution (86 mg) in acetone (20 ml) is added drop by drop. The suspension was dried in a rotative evaporator under vacuum, the temperature of the bath was 45° C. The solid obtained was air-dried at 110° C. for 2 hours.

Example 2

1.6 g of a catalyst, prepared as described in Example 1, are put inside an autoclave with 150 g of methanol and 24 ppm of HBr. The mixture was pressurized at 9.6 MPa(a) with nitrogen and stabilized at 40° C. Then the reactor was feed with the gas reaction mixture $H_2:O_2:N_2$ (3.6:46.4:50) with a total flow of 2500 mlN/min and the stirring was started up (1500 rpm) to initiate the reaction. After 2 h of the reaction a hydrogen peroxide concentration of 9.3 wt % was reached. The hydrogen peroxide selectivity was 80%.

Example 3

A hydrogen peroxide solution, prepared as described in Example 2, was used in the epoxidation of 1-octene without any kind of previous purification. 1-octene (0.1 mol), methanol (55 ml) and a hydrogen peroxide solution was prepared as described in Example 2 (4.4 g) were heated at 333 K (approximatively 60° C.). Then, 1 g of TS-1 catalyst (prepared as described in J. A. Martens, Ph. Buskens, P. A. Jacobs A. van der Pol, J. H. C. van Hooff C. Ferrini, H. W. Kouwenhoven, P. J. Kooyman and H. van Bekkum, Appl. Catal. A: General, 99, 71 (1993)) was added. The transformation of $H_2O_2$ obtained was of 93% and the efficiency of $H_2O_2$ was 90.5%, after 1.5 hours of reaction. From oct-1-ene converted the selectivity to epoxide was 50% and 50% to methyl-ethers.

Example Comparative 1

A synthetic solution of hydrogen peroxide as taught by Example 2 of U.S. patent application No. 2001/016187, 4.2 wt % $H_2O_2$ and 1% wt $H_2SO_4$ in water, was employed in the epoxidation of 1-octene using a TS-1 catalyst under the same reaction conditions of above Example 3. A 60% efficiency of $H_2O_2$ was observed. No epoxide formation was detected. From oct-1-ene converted the selectivity to methylethers (2-methoxy-octan-1-ol and 1-methoxy-octan-2-ol) was 88% and 2% to 1,2-octanediol. This comparative example teaches that hydrogen peroxide solutions obtained according to U.S. patent application No. 2001/016187 are not adequate to epoxidize alkenes without pretreatment of such solutions.

Example 4

A hydrogen peroxide solution, prepared as described in Example 2, was used in the epoxidation of 1-octene without any kind of previous purification. 0.2 moles of olefin, 11 g of 2-methyl-2-propanol and 1 g of catalyst prepared according to Example 3 of WO 99/48884 were introduced into the reactor. The mixture was heated to 80° C. and 6 g of the $H_2O_2$ solution were added drop by drop for 30 minutes. The transformation of $H_2O_2$ obtained was of 93% and efficiency of 95%, after one hour of reaction from the beginning of the addition of the hydrogen peroxide. The only product detected from 1-octene was the epoxide.

Example 5

A hydrogen peroxide solution prepared as described in Example 2 was used in the epoxidation of propylene without any kind of previous purification. This solution was diluted with tert-butanol as solvent (stream a). A stirred continuous tank reactor equipped with a filter to maintain the catalyst inside the reactor, was charged with 13.88 g of powdered catalyst, prepared according to Example 3 of WO 99/48884. The reactor was heated to 70° C., then 319.5 g/h of propylene and 222.2 g/h of stream a were fed continuously to the reactor. After 60 minutes, 96% conversion of $H_2O_2$ and 95% selectivity towards propylene oxide on the basis of hydrogen peroxide reacted.

Example 6

1 g of titanium silicalite (TS-1), the same employed in Example 3, was mixed with 50 g of a mixture consisting in 41 wt % methanol, 31 wt % water, 20 wt % cyclohexanone and 8 wt % ammonia. This mixture was suspended in a reactor an heated at reflux. Then, 3 g of the hydrogen peroxide solution prepared in Example 1 were added continuously during 5 h. The conversion of hydrogen peroxide was 100%, and the selectivity to cyclohexanone oxime was 99%.

Example 7

A hydrogen peroxide solution, prepared as described in Example 2, was used in the epoxidation of allyl alcohol without any kind of previous purification. 22.6 g of alcohol and 1 g of catalyst prepared according to Example 3 of WO 99/48884 were introduced into the reactor. The mixture was heated to 80° C. and 4 g of the $H_2O_2$ solution were added drop by drop for 30 minutes. The transformation of $H_2O_2$ obtained was of 100% and the specificity for epoxide of 99.9%, after one hour of reaction, from the beginning of the addition of the hydrogen peroxide.

Although this invention has been described broadly and also identifies specific preferred embodiments, it will be understood that modifications and variations may be within the scope of the invention as defined by the following claims.

What is claimed is:

1. A process for selective oxidation of an organic chemical compound with directly produced hydrogen peroxide, comprising:
   (i) preparing a nonacidic hydrogen peroxide solution by reacting hydrogen and oxygen in a solvent, in the presence of a first catalyst comprising at least a noble metal and/or a semi-noble metal belonging to groups VII to XI of the periodic table supported on a halogen-free acid resin;
   (ii) recovering the reaction mixture containing said nonacidic hydrogen peroxide solution; and
   (iii) contacting said nonacidic hydrogen peroxide solution with an organic chemical compound, in the presence of a second catalyst to render an oxidized product.

2. The process according to claim 1, wherein the hydrogen peroxide from the step (i) is directly used as an ingredient of the step (iii).

3. The process according to claim 1, wherein said noble or semi-noble metal is selected from the group consisting of palladium, platinum, silver, gold rhodium, iridium, ruthenium, osmium, and mixtures thereof.

4. The process according to claim 1, wherein the quantity of the noble metal and the semi-noble metal in said first catalyst ranges from 0.001% to 20% in weight with respect to the halogen-free acid resin.

5. The process according to claim 1, wherein said halogen-free acid resin is a sulphonated styrene and divinylbenzene copolymer resin.

6. The process according to claim 1, wherein the solvent used in the step (i) is selected from the group consisting of water, $C_1$–$C_{12}$ alcohols, $C_1$–$C_{12}$ glycols, and mixtures thereof.

7. The process according to claim 1, wherein a reaction temperature between the hydrogen and the oxygen in the presence of the solvent and the first catalyst ranges from −10° C. to 100° C.

8. The process according to claim 1, wherein the reaction between the hydrogen and the oxygen in the presence of the solvent and the first catalyst is carried out at a pressure above atmospheric pressure, optionally in the presence of an inert gas, and with a molar relation between the hydrogen and the oxygen in a gas phase ranging from 1/1 to 1/100.

9. The process according to claim 1, wherein the second catalyst is selected from the group consisting of titanium silicalite-1 (TS-1), titanium silicalite-2 (TS2), titanium supported on amorphous silica, and Ti-MCM-41.

10. The process according to claim 1, wherein a reaction temperature in the step (iii) ranges from −30° C. to 200° C.

11. The process according to claim 1, wherein oxidation of the organic chemical compound in the step (iii) is carried out at a pressure between 0.1 and 10 MPa.

12. The process according to claim 1, wherein oxidation of the organic chemical compound in the step (iii) is carried out in the presence of an additional solvent.

13. The process according to claim 1, wherein the organic chemical compound is an alkene.

14. The process according to claim 1, wherein the organic chemical compound is selected from the group consisting of propylene, allyl alcohol, allyl chloride, cyclohexene, cyclohexanone, benzene, phenol, and mixtures thereof.

15. The process according to claim 1, wherein the quantity of the noble metal and the semi-noble metal in said first catalyst ranges from 0.1% to 10% in weight with respect to the halogen-free acid resin.

16. The process according to claim 1, wherein a reaction temperature between the hydrogen and the oxygen in the presence of the solvent and the first catalyst ranges from 10° C. to 75° C.

17. The process according to claim 1, wherein the reaction between the hydrogen and the oxygen in the presence of the solvent and the first catalyst is carried out at a pressure between 2 to 30 MPa, optionally in the presence of an inert gas, and with a molar relation between the hydrogen and the oxygen in a gas phase ranging from 1/1 to 1/100.

18. The process according to claim 1, wherein a reaction temperature in the step (iii) ranges from −10° C. to 150° C.

19. The process according to claim 1, wherein oxidation of the organic chemical compound in the step (iii) is carried out at a pressure between 0.1 and 5 MPa.

20. A process for selective oxidation of an organic chemical compound with directly produced hydrogen peroxide, comprising:

(i) preparing a nonacidic hydrogen peroxide solution by reacting hydrogen and oxygen in an organic solvent, in the presence of a first catalyst comprising at least a noble metal and/or a semi-noble metal belonging to groups VII to XI of the periodic table supported on a halogen-free acid resin;

(ii) recovering the reaction mixture containing said nonacidic hydrogen peroxide solution; and (iii) contacting said nonacidic hydrogen peroxide solution with an organic chemical compound, in the presence of a second catalyst to render an oxidized product.

* * * * *